United States Patent [19]

Garrou et al.

[11] 4,299,777
[45] Nov. 10, 1981

[54] PREPARATION OF CYANO ACETALS

[75] Inventors: Philip E. Garrou, Holliston; Robert A. Dubois, Franklin; Bart J. Bremmer, Ashland, all of Mass.

[73] Assignee: The Dow Chemical Company, Midland, Mich.

[21] Appl. No.: 159,038

[22] Filed: Jun. 13, 1980

[51] Int. Cl.$^3$ ................. C07C 120/00; C07C 121/46; C07C 121/16
[52] U.S. Cl. ............................ 260/465.6; 260/340.7; 260/340.9 R; 260/464
[58] Field of Search ............ 260/464, 340.7, 340.9 R, 260/465.6; 568/594

[56] References Cited

U.S. PATENT DOCUMENTS

| | | | |
|---|---|---|---|
| 2,506,571 | 5/1950 | Barrick et al. | 260/465.6 |
| 3,466,317 | 9/1969 | Kuper | 260/465.6 |
| 3,520,914 | 7/1970 | Kuper | 260/465.6 |
| 3,546,269 | 12/1970 | Wakamatsu et al. | 260/465.6 |
| 4,201,868 | 5/1980 | Slinkard | 568/594 X |

*Primary Examiner*—Joseph P. Brust
*Attorney, Agent, or Firm*—Douglas N. Deline

[57] ABSTRACT

Cyano acetals prepared by the reaction of an alcohol with a nitrile CO and $H_2$ in the presence of a $Co_2(CO)_8$ catalyst are more selectively produced at elevated temperatures by the addition of an effective amount of a cyano alkyl amine or carboxy alkyl amine promoter.

7 Claims, No Drawings

PREPARATION OF CYANO ACETALS

BACKGROUND OF THE INVENTION

This invention relates to the production of cyano acetals. More particularly it relates to a method of improving the selectivity of formation of cyano acetals by the catalytic reaction of a nitrile, an alcohol, CO and $H_2$.

It is known to synthesize acetals containing a cyano group by hydroformylation. For example in U.S. Pat. No. 3,466,317 a process is disclosed wherein acetonitrile or alkyl-substituted derivatives thereof are reacted with a lower alkanol, CO and $H_2$ in the presence of a Group VIII metal-containing, hydrogenating catalyst and an acid at pressures of at least 60 atmospheres. The presence of the acid advantageously permitted the use of lower operating pressures.

Known methods of synthesis however continue to be unsatisfactory because of a tendency of the generally used $Co_2(CO)_8$ catalyst to become unstable at elevated temperatures thereby promoting the formation of undesirable by-products.

SUMMARY OF THE INVENTION

It has now been discovered that certain cyano or carboxy-substituted amine compounds may be beneficially added to a $Co_2(CO)_8$ catalyzed hydroformylation of compounds of the formula $H_2C=CR'-C\equiv N$ where R' is H or $C_{1-4}$ alkyl. The cyano- or carboxy-substituted amines stabilize the catalyst at elevated temperatures thereby promoting the formation of desired 3-cyano acetals. Without the addition of such amines, desirable conversion rates obtainable by operating at elevated temperatures result in a disadvantageous loss of selectivity in product formation. The reaction involved is graphically represented by

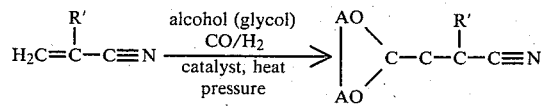

A represents the remnant of the alcohol which in the event a glycol is employed may optionally be represented as A—A.

DETAILED DESCRIPTION OF THE INVENTION

The cyano- or carboxy-substituted amine compounds suitable for use as catalyst promoters according to the instant invention are of the formula $HNR_mX_n$ where R is hydrogen, or a $C_{1-4}$ radical selected from alkyl and amino alkyl; X is $(CH_2)_yCN$ or $(CH_2)_yCOOH$ wherein y is an integer from one to three; and m and n are integers from zero to two provided that n is at least one and $n+m=2$. They are combined with $Co_2(CO)_8$ in an amount sufficient to improve the selectivity of 3-cyano acetal formation. Suitably the promoter may be used in a weight ratio of catalyst/promoter from 10/1—1/10; preferably from 1/1 to ½. The catalyst and promoter may be combined prior to introduction into a suitable reactor or the catalyst may first be added followed by subsequent addition of the cyano amine to produce the desired catalyst composition in situ.

The alcohols commonly employed in hydroformylation of this nature are saturated primary or secondary hydroxy-containing compounds selected from alkanols glycols and cyclohexanol. Included are methanol, ethanol, 1-propanol, 2-propanol, 1-butanol, 2-butanol, cyclohexanol, ethylene glycol, propylene glycol and the like. Preferred is a primary alkanol of 1-4 carbon atoms per molecule.

The pressures employed in the reaction may be as low as 60 atmospheres. Upper limits are determined by the reactor design limits. Preferred are pressures from about 70 atmospheres to about 200 atmospheres.

The temperatures employed may range from about 75° C. to about 200° C. depending on the degree of selectivity to cyano acetal formation and rate of reactant consumption that is acceptable. Generally at temperatures above about 100° C. the greater selectivity afforded by utilization of the present promoters is measurably noticeable. At still higher temperatures the beneficial effect of the promoters is significant.

The hydroformylation process is carried out by mixing the reactants in a suitably designed pressure reactor containing the catalyst and heating to the desired reaction temperature. Suitably the catalyst may be present in an amount equal to at least 0.1 weight percent based on the nitrile reactant, and preferably between 1 and 15 weight percent. Generally, the amount of alcohol used is present in such proportion that at least two active hydroxyl groups per one molecule of the nitrile are available.

Carbon monoxide and hydrogen are added to the reaction vessel to produce the desired reaction pressure. The molar ratio of carbon monoxide to hydrogen may range from about 0.5 to about 2. In general a molar ratio of about 1 is utilized. Desirably the amount of carbon monoxide initially present is at least molarly equivalent and preferably in excess of the amount of nitrile employed.

The aforementioned operating conditions of the reaction as well as the use of the cyano acetals so produced as selective solvents for hydrocarbon extractions has previously been described in U.S. Pat. No. 3,466,317.

SPECIFIC EMBODIMENTS

The following examples are provided as illustrative of the present invention and are not to be construed as limiting. The term selectivity occurring in the specification and claims defines the amount of 3-cyano acetal formed based on nitrile starting reactant.

EXAMPLE 1

In a 300 ml stainless steel pressure reactor were placed acrylonitrile (2 g), methanol (8 ml), $Co_2(CO)_8$ (0.13 g) and $HN(CH_2CN)_2$ (0.07 g). The vessel was pressurized to about 100 atmospheres with CO and $H_2$ in a 1:1 mixture. The reaction mixture was maintained at about 145° C. for about 6 hours. After cooling and release of pressure a trace of 1,2,3,4-tetrahydronaphthalene was added for an internal standard and the product analyzed by gas chromatography. Results are provided in Table I along with comparative results of similar experiments conducted at various temperatures and pressures with and without the presence of promoters.

TABLE I

| Promoter | Temp °C. | Pressure (atm) | % Selectivity |
|---|---|---|---|
| — | 100 | 170 | 90 |
| — | 145 | 170 | 42 |
| $HN(CH_2CN)_2$ | 100 | 100 | 95 |
| $HN(CH_2CN)_2$ | 145 | 100 | 84 |

TABLE I-continued

| Promoter | Temp °C. | Pressure (atm) | % Selectivity |
|---|---|---|---|
| $HN(CH_2CH_2CN)(CH_2CH_2NH_2)$ | 145 | 110 | 75 |
| $HN(CH_2COOH)_2$ | 145 | 100 | 52 |
| $HN[C_2H_4N(CH_3)_2]CH_3$* | 130 | 120 | 0 |
| N-methyl pyrrolidine* | 130 | 170 | 0 |
| N-vinyl pyridine* | 120 | 135 | 10 |

*For comparative purposes not considered part of the invention.

The results indicate that presence of a cyanoalkyl amine or carboxy alkyl amine promoter significantly improved the selectivity of formation of the desired cyanoacetal at elevated temperatures. The preferred promoter is dicyano methylamine. The results also indicate that certain amine compounds produce a loss of selectivity. The favorable activity of the compounds of the invention is therefore considered to be surprising.

What is claimed is:

1. In a process for the preparation of a 3-cyano acetal by reacting a reaction mixture containing a nitrile represented by the formula $CH_2=CR'-C\equiv N$ where R' is hydrogen or $C_{1-4}$ alkyl; a saturated primary or secondary hydroxy-containing compound selected from the group consisting of $C_{1-6}$ alkanols and cyclohexanol; carbon monoxide; and hydrogen in the presence of $Co_2(CO)_8$ catalyst at a pressure of at least 60 atmospheres and a temperature from about 75° C. to about 200° C., the improvement comprising adding to the reaction mixture an effective amount to increase selectivity of 3-cyano acetal formation of a catalyst promoter of the formula $HNR_mX_n$ where R is hydrogen or a $C_{1-4}$ radical selected from alkyl and aminoalkyl; X is $(CH_2)_yCN$ or $(CH_2)_yCOOH$ wherein y is an integer from 1 to 3; and m and n are integers from 0 to 2, provided that n is at least 1, and $m+n=2$.

2. The process according to claim 1 wherein the nitrile is acrylonitrile.

3. The process according to claim 1 wherein the hydroxy-containing compound is $C_{1-4}$ primary alkanol.

4. The process according to claim 1 wherein the reaction is conducted at a pressure from about 70 atmospheres to about 200 atmospheres.

5. The process according to claim 4 wherein the temperature is above about 100° C.

6. The process according to claims 1, 2, 3, 4 or 5 wherein the promoter is dicyano methylamine.

7. The process according to claim 6 wherein the promoter is added to the reaction in a weight ratio of catalyst to promoter of from about 10/1 to about 1/10.

* * * * *

UNITED STATES PATENT AND TRADEMARK OFFICE
CERTIFICATE OF CORRECTION

PATENT NO. : 4,299,777
DATED : November 10, 1981
INVENTOR(S) : Philip E. Garrou, Robert A. Dubois, Bart J. Bremmer It is certified that error appears in the above—identified patent and that said Letters Patent is hereby corrected as shown below:

Col. 1, line 21, "$CO_2(CO)_8$" should read -- $Co_2(CO)_8$ --.

Signed and Sealed this

Twenty-fifth Day of May 1982

[SEAL]

Attest:

GERALD J. MOSSINGHOFF

*Attesting Officer*  *Commissioner of Patents and Trademarks*